US006294692B1

(12) United States Patent
Hussenet et al.

(10) Patent No.: US 6,294,692 B1
(45) Date of Patent: Sep. 25, 2001

(54) PROCESS FOR PRODUCING N-FORMYLLEUCINE OF HIGH PURITY

(75) Inventors: Patricia Hussenet, Juvisy; Philippe Le Goff, Strasbourg; Gérard Sennyey, Saint-Aubin; Charles-Henry Vincent, Precy Sur Oise, all of (FR)

(73) Assignee: Isochem, Paris (FR)

( * ) Notice: Subject to any disclaimer, the term of this patent is extended or adjusted under 35 U.S.C. 154(b) by 0 days.

(21) Appl. No.: 09/460,991

(22) Filed: Dec. 15, 1999

(30) Foreign Application Priority Data

Dec. 30, 1998 (FR) .................................................. 98 16611

(51) Int. Cl.⁷ ........................ C07C 229/08; C07C 229/10
(52) U.S. Cl. ............................................. 562/567; 562/553
(58) Field of Search ...................................... 562/553, 567

(56) References Cited

U.S. PATENT DOCUMENTS 4,789,757   12/1988   Carter ................................. 562/445

FOREIGN PATENT DOCUMENTS 0 080 119 A1   6/1983   (EP) .

Primary Examiner—Gary Geist
Assistant Examiner—Leigh C. Maier
(74) Attorney, Agent, or Firm—Oliff & Berridge, PLC

(57) ABSTRACT

A process for producing N-formylleucine includes reacting leucine with formamide, precipitating the N-formylleucine, once the reaction is complete, at a temperature of approximately 0° to 40° C., by mixing the reaction medium with water and an acid, so that the final pH of the mixture is approximately 2 to 3, wherein the amount of water used in between approximately 1.5 and 5 parts per part by weight of starting formamide.

11 Claims, No Drawings

PROCESS FOR PRODUCING N-FORMYLLEUCINE OF HIGH PURITY

The invention relates to a process for producing N-formylleucine of high purity.

N-Formylleucine, composed of the leucine molecule with one of the hydrogen atoms attached to the nitrogen replaced by a formyl group, is a known compound used in particular in carrying out peptide syntheses.

Various processes for the formylation of amines, in particular of the amine groups of amino acids, are known. Industrially, amino acids are generally N-formylated by the action of formic acid or of an alkali metal formate. However, these processes have disadvantages. Troublesome impurities are also formed, in particular because the reaction is carried out in the presence of acetic anhydride. The latter also reacts with the amino acids and a certain amount of N-acetylated amino acid is then always formed, which product is difficult to separate from the N-formylated amino acid.

Another formulation process has been disclosed in U.S. Pat. No. 4,789,757. It consists in reacting the amino acid with a very large excess of formamide. Thus, in the majority of examples, a molar amount of formamide 10 times greater than that of the amino acid is used. N-Formylaspartic acid, N-formylglycine, N-formylalanine and N-formylphenylalanine are thus prepared. However, the methods for isolating these N-formylated derivatives from the reaction mixture and for recovering them with the minimum possible in the way of impurities are not disclosed.

For some applications, such as applications in the pharmaceutical or food field, it is necessary to have available an N-formylleucine of high purity. If the formylation of leucine is carried out by the process described above by means of formamide, the N-formylleucine obtained will certainly not be contaminated by impurities such as N-acetylated derivatives but it will generally still comprise unreacted leucine, isoleucine and other impurities present in the starting material, and the reaction products of these impurities with formamide.

The subject-matter of the invention is consequently a process for producing N-formylleucine having a purity at least equal to 98%.

The process according to the invention consists in preparing N-formylleucine by reaction of leucine with formamide and is characterized in that, when the reaction is complete, the N-formylleucine is precipitated, at a temperature of approximately 0° to 40° C., by mixing the reaction medium with water and an acid, so that the final pH of the mixture is approximately 2 to 3.

It has also been found that the process is improved if the reaction of leucine with formamide is carried out in the presence of formic acid and in particular in the presence of approximately 0.1 to 2 mol of formic acid per mole of leucine.

The process of the invention makes it possible to obtain N-formylleucine with the desired purity, at least equal to 98%, and with a good yield, generally of the order of 80 to 90%.

The leucine which is used as starting compound is a known compound which is available commercially in the D, L and DL forms. It generally comprises isoleucine as the main impurity.

The N-formylation reaction can be carried out as shown in U.S. Pat. No. 4,789,757 with a considerable excess of formamide, generally with approximately 10 mol of formamide per mole of amino acid.

However, it has now been found that it is preferable not to use a very large excess of formamide and that an amount of formamide of less than 4 mol per mole of leucine and in particular of: approximately 1.5 to 3.5 mol per mole of leucine is highly suitable.

It is also advantageous to carry out the N-formylation reaction in the presence of formic acid. Use is preferably made of approximately 0.5 to 1 mol of formic acid per mole of leucine.

The reaction is carried out by heating the mixture, composed of formamide and leucine and, optionally, formic acid, at a temperature of between approximately 80° C. and 110° C., preferably between approximately 90° C. and 100° C., and preferably under an inert atmosphere, such as under a nitrogen atmosphere. It generally lasts from 1 to several hours.

When it is complete, it is then advantageous, if an amount of formamide greater than the preferred amount has been used, to distill off a portion of the formamide remaining in the medium after the reaction, so as not to complicate the precipitation operation because of this excess of reactant.

The N-formylleucine is subsequently precipitated. To do this, use is made of a large amount of water, preferably of between approximately 1.5 and 5 parts per part by weight of starting formamide, and of an acid, in particular an inorganic acid, for example hydrochloric or sulphuric acid, so that there is a pH of approximately 2 to 3, preferably of approximately 2 to 2.5, at the end of the precipitation.

According to one alternative form, in carrying out the precipitation operation, acid is first of all added to the water needed for the precipitation, in order for its pH to be acidic, preferably of approximately 2 to 3, and then the reaction medium and the acidified water are mixed, preferably by pouring the reaction medium into the acidified water or by simultaneously pouring the reaction medium and the acidified water into a reactor. Throughout the duration of the precipitation, the mixture is preferably maintained at a pH of approximately 2 to 3 and more particularly of approximately 2 to 2.5 by adding acid to the mixture, if necessary. According to this alternative form, it is also advantageous, before carrying out the precipitation operation, to dilute the reaction mixture with water, for example in an amount of between approximately 0.2 and 0.4 part per part by weight of formamide.

According to another alternative form, the reaction medium is first of all mixed with water and then the pH of the mixture is brought to and maintained at approximately 2 to 3, preferably approximately 2 to 2.5, by addition of acid.

The acid used is more particularly sulphuric acid.

It is also important for the temperature during the precipitation to be maintained between approximately 0° C. and 40° C., preferably between approximately 5° C. and 20° C.

The N-formylleucine spontaneously crystallizes but it is also possible to introduce a seed in order to promote the crystallization.

On completion of the crystallization, the N-formylleucine crystals are recovered using one of the usual methods. The crystals obtained in particular have a size sufficient to be easily filtered off, washed and dried.

The dry N-formylleucine yield is generally greater than 80%.

The purity of the N-formylleucine is equal to or greater than 98%, often even greater than 99%.

The N-formylleucine obtained according to the process of the invention can be used directly as intermediate in carrying out syntheses of peptides or in preparing pharmaceutical products.

The examples which follow illustrate the invention without, however, limiting it.

EXAMPLE 1

165.2 g of L-leucine and 821.7 g of formamide are introduced, under a nitrogen atmosphere, into a reactor equipped with a stirrer system. The mixture is heated at 100° C. for approximately 6 hours. Approximately 513 g of formamide are then removed by distillation under a pressure of 20 –30 mm of mercury and at a pot temperature of 50°–60° C. 1082 g of water are subsequently added to the mixture. It is cooled to 20°–25° C. It is then acidified to pH 2.5 with sulphuric acid. It is stirred for 2 hours at approximately 20° C. and then for one hour at 5° C. Filtration is carried out and the cake is rinsed with 100 g of water at pH 2. It is dried under vacuum. 180.3 g of N-formyl-L-leucine are thus obtained (90% yield) with an optical rotation $[\alpha]_D^{20}=-17.7°$ (c=1 in ethanol), i.e. a purity of 98.3%.

It is determined by chromatography (TLC or GC) that less than 0.1% by weight of leucine and less than 0.01% by weight of isoleucine remain.

EXAMPLE 2

520 kg (11.55 kmol) of formamide and 500 kg (3.81 kmol) of L-leucine are introduced, under a nitrogen atmosphere, into a reactor equipped with a stirrer system. The mixture is heated to a temperature of between 96° C. and 101° C. and is maintained at this temperature for 10 hours. It is converted into a clear orange-yellow solution. 150 litres of deionized water are then added at approximately 20° C. The N-formyl-L-leucine is then precipitated by pouring the mixture, over approximately 1 hour, into 1500 litres of water acidified to a pH of 2 to 3 by means of 55% sulphuric acid, this pH being maintained throughout the duration of the operation by addition of 55% sulphuric acid and the temperature being maintained between 0° C. and 35° C.

The N-formyl-L-leucine gradually crystallizes. When all the mixture has been poured into the water, the medium is maintained for a further 4 hours at a pH of 2 to 2.5 and at a temperature of 15° C.

The crystals formed are collected using a centrifuge, are washed several Limes with neutral water and are dried in an oven. 490 kg (81% yield) of N-formyl-L-leucine are obtained with the following characteristics:

Water content: 0.08%,

Melting point: 139° C.,

Purity: 99.8% (determined by high pressure liquid chromatography, HPLC, or by titration).

EXAMPLE 3

1 kg of L-leucine, 0.68 kg of formamide and 0.35 kg of formic acid are introduced, under a nitrogen atmosphere, into a reactor equipped with a stirrer system.

The mixture is heated at approximately 90° C. for 3 to 4 hours. 2 litres of water are subsequently added. The mixture is cooled to 15° C.

0.62 kg of 55% sulphuric acid is then introduced into the mixture and a pH of 2.3 is obtained. Stirring of the mixture is continued for 30 minutes at 15° C. The crystals formed are collected by centrifuging, are washed several times with water and are dried. 1.05 kg (86% yield) of N-formyl-L-leucine are obtained with a purity of 98% (determined by HPLC).

What is claimed is:

1. Process for producing N-formylleucine, comprising:
   reacting leucine with formaldehyde in the presence of formic acid;
   precipitating the N-formylleucine, once the reaction is complete, at a temperature of approximately 0° to 40° C., by mixing the reaction medium with water and an acid, so that the final pH of the mixture is approximately 2 to 3, wherein the amount of water used when mixing the reaction medium is between approximately 1.5 and 5 parts per part by weight of starting formamide.

2. The process according to claim 1 wherein the amount of formamide reacted with leucine is less than about 4 mol per mole of leucine.

3. The process according to claim 1, wherein, in carrying out the precipitation, the water needed for the precipitation is acidified by adding acid before mixing the water with the reaction medium.

4. The process according to claim 3, wherein before carrying out the precipitation operation, the reaction mixture is diluted with water.

5. The process according to claims 1 wherein in carrying out the precipitation, water is first mixed with the reaction medium and then the pH of the mixture is brought to and maintained at approximately 2 to 3 by addition of acid.

6. The process according to claim 1, wherein during the precipitation operation, the pH is, at least at the end of the precipitation, maintained between approximately 2 and 2.5.

7. The process according to claim 1, wherein the temperature of the precipitation stage is between approximately 5° C. and 20° C.

8. The process according to claim 1 wherein leucine and formamide are reacted at a temperature of between approximately 80° C. and 110° C.

9. The process according to claim 1, wherein the reaction is carried out in the presence of approximately 0.1 to 2 mol of formic acid per mole of leucine.

10. The process according to claim 1, wherein the amount of formamide reacted with leucine is less than 3.5 mole per mole of leucine.

11. The process according to claim 1, wherein the amount of formamide is less than about 4 mole per mole of leucine.

* * * * *